United States Patent
Cai et al.

(10) Patent No.: US 9,814,655 B2
(45) Date of Patent: Nov. 14, 2017

(54) DENTAL FILLER AND COMPOSITIONS

(71) Applicant: DENTSPLY International Inc., York, PA (US)

(72) Inventors: Yang Cai, Middletown, DE (US); Xiaoming Jin, Middletown, DE (US); Xin Huo, Dover, DE (US)

(73) Assignee: Dentsply International Inc., York, PA (US)

( * ) Notice: Subject to any disclaimer, the term of this patent is extended or adjusted under 35 U.S.C. 154(b) by 277 days.

(21) Appl. No.: 14/210,518

(22) Filed: Mar. 14, 2014

(65) Prior Publication Data

US 2014/0275326 A1  Sep. 18, 2014

Related U.S. Application Data

(60) Provisional application No. 61/783,038, filed on Mar. 14, 2013.

(51) Int. Cl.
| | |
|---|---|
| *A61K 6/08* | (2006.01) |
| *A61K 6/00* | (2006.01) |
| *A61K 6/02* | (2006.01) |
| *A61K 6/083* | (2006.01) |

(52) U.S. Cl.
CPC .......... *A61K 6/0091* (2013.01); *A61K 6/0008* (2013.01); *A61K 6/0073* (2013.01); *A61K 6/0088* (2013.01); *A61K 6/023* (2013.01); *A61K 6/024* (2013.01); *A61K 6/025* (2013.01); *A61K 6/0215* (2013.01); *A61K 6/0235* (2013.01); *A61K 6/083* (2013.01)

(58) Field of Classification Search
CPC ................................................... A61K 6/0073
See application file for complete search history.

(56) References Cited

U.S. PATENT DOCUMENTS

| | | | |
|---|---|---|---|
| 2003/0060533 A1* | 3/2003 | Ohtsuki | A61K 6/0017 523/115 |
| 2010/0035214 A1* | 2/2010 | Reynaud | A61C 13/30 433/220 |
| 2010/0130346 A1* | 5/2010 | Laine | B82Y 30/00 501/105 |
| 2012/0004342 A1* | 1/2012 | Lambert | C04B 14/041 523/115 |

OTHER PUBLICATIONS

Darbandi, M.; Nann, T. Chem. Commun., 2006, 776-778. Royal Society of Chemistry.*

* cited by examiner

*Primary Examiner* — Michael Pepitone
(74) *Attorney, Agent, or Firm* — Leana Levin; Douglas J. Hura; David A. Zdorne

(57) ABSTRACT

Described herein is a dental filler material having a core made of a core material and a shell made of a shell material, where the shell material coats or covers at least a portion of the core.

17 Claims, No Drawings

DENTAL FILLER AND COMPOSITIONS

The patent application claims priority to Provisional Application No. 61/783,038, filed Mar. 14, 2013.

TECHNICAL FIELD

Described herein are dental filler materials having a particular configuration. That is, described herein are dental filler materials suitable for use in dental restoratives, adhesives, and other dental compositions, where the dental filler has a core made of a core material and is coated at least partially by a shell material.

BACKGROUND

Various dental materials having dental materials are known in the art. For example, U.S. Pat. No. 6,730,156 describes a filler comprising a substantially amorphous cluster comprising non-heavy metal oxide particles and heavy metal oxide. The filler can be mixed into a hardenable resin to provide radiopaque dental materials having desirable strength and aesthetic character.

U.S. Pat. No. 6,572,693 describes a material having a hardenable resin; and a filler comprising (i) clusters of nano-sized particles, the clusters comprising non-heavy metal oxide particles and heavy metal oxides, and being not fully densified particles and (ii) non-agglomerated nano-sized particles selected from the group consisting of non-heavy metal oxide particles, heavy metal oxide particles, and combinations thereof. The material is suitable for use as dental materials.

U.S. Pat. No. 7,981,513 describes a dental filler having the optical and/or mechanical properties satisfying the requirements to a dental material, a method for producing the dental filler, and a dental composite material containing the dental filler. The dental filler comprises microparticles of amorphous inorganic oxide constituted by at least silica-based fine particles covered with a composite oxide comprising zirconium, silicon and oxygen. The dental composite material contains the dental filler and a hardenable resin selected from an acrylic resin, a methacrylic resin, an epoxy resin, a vinyl resin and a urethane resin.

SUMMARY

In embodiments, disclosed is an agglomerated filler material comprising a core and a shell, wherein the core is made of a core material and the shell is made of a shell material, such that the core material and the shell material may be a same material or a different material, wherein the shell material attaches to the core material via electrostatic forces, wherein the core material is positively or negatively charged and the shell material is an opposite charge of the core material, wherein a surface area of the agglomerated filler material is from about 1 $m^2/g$ to about 200 $m^2/g$.

In further embodiments, disclosed is a dental material comprising a resin, an initiator system, and a filler material, wherein the filler material comprises a core and a shell, wherein the core is made of a core material and the shell is made of a shell material, such that the core material and the shell material may be a same material or a different material, wherein the shell material attaches to the core material via electrostatic forces, wherein the core material is positively or negatively charged and the shell material is an opposite charge of the core material, wherein a surface area of the filler material is from about 1 $m^2/g$ to about 200 $m^2/g$.

DETAILED DESCRIPTION

Described herein is a novel dental filler having a core and shell configuration. The core and shell may comprise a variety of oxides, and the core and shell may be comprised of the same materials, differing materials, or even overlapping compositions. The dental filler described herein is suitable for use in any dental material, such as, dental adhesives, artificial crowns, fillings, casting materials, cavity liners, cements, coating compositions, orthodontic adhesives, restoratives, prostheses and sealants.

As described herein, the agglomerated filler material may be made by assembling a core material with a shell material then further agglomerating together by a thermal treatment from about 300° C. to about 900° C. in order to strengthen the agglomeration degree such that the desired particle size and performance described herein may be achieved.

The formed agglomerated dental filler may have a mean particle size of from about 600 nm to about 50 μm, such as a mean particle size of from about 900 nm to about 40 μm or from about 2 μm to about 30 μm.

Suitable core materials include any mixed oxides having a primary particle size of from about 300 nm to about 2 μm, such as a primary particle size of from about 300 nm to about 1 μm. The core material may be entirely amorphous or partially crystalline. The shape of the core material may be either regular or irregular.

The shell material may be any mixed oxide, the same as, substantially the same as, substantially different from or completely different from the material of the core material. The shell material may have a particle size of from about 1 nm to about 300 nm, such as a particle size of from about 15 nm to about 250 nm or from about 30 nm to about 200 nm. The shell material may be entirely amorphous or partially crystalline.

The shell material may entirely cover the entire surface of the core, substantially cover the entire surface of the core or only partially cover the surface of the formed core. The shell material should cover at least about 25 percent of the surface of the core, or from about 30 percent to about 85 percent of the surface of the core or from about 40 percent to about 75 percent of the surface of the core.

Suitable mixed oxides for both the core material and shell material include NaO, $K_2O$, $Fe_2O_3$, $SiO_2$, BaO, $Al_2O_3$, $B_2O_3$, $TiO_2$, $ZrO_2$, CaO, MgO, $Y_2O_3$, SrO, $Yb_2O_3$, $SnO_2$, $GeO_2$ and any mixture thereof. Both the core material and shell material may optionally further include fluorine.

As used herein, the shell refers to the particles or shell material that forms at least a partial coating or covering the core or core material. As described herein, the core material has a greater particle size than the shell material. The particles of the shell material are attracted to the core due to electrostatic forces such that as more particles of the shell material are attracted to the core and coat the core, the surface area of the filler material increases.

The surface area of the formed agglomerated filler material, that is the core/shell configuration of the described dental filler, may be in a range of from about 1 $m^2/g$ to about 200 $m^2/g$, such as from about 3 $m^2/g$ to about 100 $m^2/g$ or from about 5 $m^2/g$ to about 50 $m^2/g$.

The agglomerated filler material described herein may be formed by dispersing a suitable core material having a mean particle size as described above in distilled water. This core material dispersion is then stirred in the water using a mechanical mixer for a time of from about 30 minutes to about 5 hours. The core material dispersion is then charged into a mixture of shell material at a rate of from about 15 mL/minute to about to about 65 mL/minute. The dispersion of core material and shell material is then stirred for an additional time of from about 15 minutes to about 2 hours. The resulting suspension is dried, and the coarse particulates having a mean particle size of from 2 mm to 2 cm are milled to obtain a fine particulate having a mean particle size of from 5 μm to 20 μm. The milled material is then heated to a temperature of from about 500° C. to about 900° C., such as from about 700° C. to about 850° C., in order to reduce the surface area. In other words, the milled material prior to heating has a greater surface area than the desired surface area as described above. Unlike the prior art, this heat treatment reduces the surface size of the filler material described herein by about 35% to about 90%, such as from about 45% to about 80%, such that the final surface area of the filler material is from about 1 $m^2/g$ to about 200 $m^2/g$, such as from about 3 $m^2/g$ to about 100 $m^2/g$ or from about 5 $m^2/g$ to about 50 $m^2/g$. The white powder obtained after the heating step has a mean particle size of from about 600 nm to about 50 μm, such as a mean particle size of from about 900 nm to about 40 μm or from about 2 μm to about 30 μm. This white powder may then be silanated using any known silanation method to a level of from about 0.1% to about 20% silanation, such as from about 0.5% to about 15% or from about 1% to about 10% silanation.

The dental fillers disclosed herein may be mixed with a hardenable resin to provide dental materials with improved handling, strength, polishability, wear and stain resistance. The hardenable resin which may be used in the present disclosure includes, but not limited to, acrylic resin, methacrylic resin, epoxy resin, vinyl resin, urethane resin and/or a combination. As one of ordinary skill will understand, the dental composite having the hardenable resin may also include an initiator system, which initiates polymerization by radiation, heat, or a chemical reaction. Such dental composite materials may contain the dental filler disclosed herein in amounts of from about 20% to about 90% by weight of the dental composite, and at least one hardenable resin in an amount of from about 10% to about 80% by weight of the dental composite. The dental filler disclosed herein may be used alone in the dental composite or combined with other known dental filler materials in the dental composite. Any other known dental filler material is suitable for use herein so long as the other dental filler includes discrete particles having a mean particle size of from about 0.01 μm to about 2 μm. In order to obtain the desired, improved performance of a dental composite, the agglomerated dental filler disclosed herein should be at least 10% by weight of the total filler mixture.

The formed agglomerated filler material described herein improves dental composite handling properties, such as stiffness and stickiness. At the same time, the dental material described herein is capable of providing good polishability because the primary particle size of the core material and shell material may be less than 2 μm, such as less than 1 μm. If properly picked, the core and shell materials may results in a dental filler that may also improve the wear resistance and mechanical strength of a formed dental composite, as well. The composite with such new filler also presents improved stain resistance as compared to known composites, such as 3M Filtek Supreme Ultra with nanocluster filler technology.

EXAMPLES

Filler Material Composition

An example of the dental filler material (filler example 1) before silanation had the following composition:

TABLE 1

| Filler example 1 | Percentage (%) |
| --- | --- |
| SiO2 | 48-57 |
| BaO | 15-25 |
| $B_2O_3$ | 5-15 |
| $Al_2O_3$ | 17-28 |
| F | 0-2 |

Making the Dental Filler Material

Filler Example 2

Into a glass container, was placed about 200 g of 0.4 micron Barium-glass and 1,000 g distilled water. The barium-glass was dispersed in water by stirring with a mechanical mixer for about 2 hours. After dispersion, the barium glass had a mean particle diameter of from about 0.6 microns to about 0.7 microns. The barium-glass dispersion was then pumped into about 700 g of a stirred colloidal mixture of silica and alumina in water, about 15% solids with a mean diameter of from about 115 nm to about 150 nm, at a rate of about 35 mL/min to about 45 mL/min. After addition, the dispersion was stirred for about an additional 30 minutes. The suspension was then dried in a forced air oven. The coarse particulates obtained were ball-milled milled for about 8 hours to obtain a fine particulate. The milled material was then placed into a crucible and heated to a temperature of about 725° C. for two hours. After this treatment the white powder obtained had a mean particle diameter of from about 9 microns to about 11.5 microns.

To make Filler Example 2, the unsilanated Filler Example 1 was silanated by tumbling about 100 g of Filler Example 1 with about 4 weight percent silane and 0.5 weight percent acetic acid solution. The mixture or slurry was then dried in an oven at about 90° C. to obtain Filler Example 2 in powder form.

Filler Example 3

Into a glass container, was placed about 200 g of 0.4 micron Barium-glass and 1,000 g distilled water. The barium-glass was dispersed in water by stirring with a mechanical mixer for about 2 hours. After dispersion, the barium glass had a mean particle diameter of from about 0.6 microns to about 0.7 microns. The barium-glass dispersion was then pumped into about 700 g of a stirred colloidal mixture of silica and alumina in water, about 15% solids with a mean diameter of from about 115 nm to about 150 nm, at a rate of about 35 mL/min to about 45 mL/min. After addition, the dispersion was stirred for about an additional 30 minutes. The suspension was then dried in a forced air oven. The coarse particulates obtained were ball-milled milled for about 8 hours to obtain a fine particulate. The milled material was then placed into a crucible and heated to a temperature of about 850° C. for two hours. After this treatment the white powder obtained had a mean particle diameter of from about 4 microns to about 7 microns.

The resulting white powder was silanated by tumbling about 100 g of the white powder with about 4 weight percent silane and 0.5 weight percent acetic acid solution. The mixture or slurry was then dried in an oven at about 90° C. to obtain Filler Example 3 in powder form.

Filler Example 4

Into a glass container, was placed about 200 g of 0.4 micron Barium-glass and 1,000 g distilled water. The barium-glass was dispersed in water by stirring with a mechanical mixer for about 2 hours. After dispersion, the barium glass had a mean particle diameter of from about 0.6 microns to about 0.7 microns. The barium-glass dispersion was then pumped into about 700 g of a stirred colloidal mixture of silica and zirconia in water, about 15% solids with a mean diameter of from about 115 nm to about 150 nm, at a rate of about 35 mL/min to about 45 mL/min. After addition, the dispersion was stirred for about an additional 30 minutes. The suspension was then dried in a forced air oven. The coarse particulates obtained were ball-milled milled for about 8 hours to obtain a fine particulate. The milled material was then placed into a crucible and heated to a temperature of about 750° C. for two hours. After this treatment the white powder obtained had a mean particle diameter of from about 1 microns to about 3 microns.

The resulting white powder was silanated by tumbling about 100 g of the white powder with about 4 weight percent silane and 0.5 weight percent acetic acid solution. The mixture or slurry was then dried in an oven in an oven at about 90° C. to obtain Filler Example 4 in powder form.

Filler Example 5

Into a glass container, was placed about 200 g of 0.4 micron Barium-glass and 1,000 g distilled water. The barium-glass was dispersed in water by stirring with a mechanical mixer for about 2 hours. After dispersion, the barium glass had a mean particle diameter of from about 0.6 microns to about 0.7 microns. The barium-glass dispersion was then pumped into about 700 g of a stirred colloidal mixture of silica and alumina in water, about 15% solids with a mean diameter of from about 115 nm to about 150 nm, at a rate of about 35 mL/min to about 45 mL/min. After addition, the dispersion was stirred for about an additional 30 minutes. The suspension was then dried in a forced air oven. The coarse particulates obtained were ball-milled milled for about 8 hours to obtain a fine particulate. The milled material was then placed into a crucible and heated to a temperature of about 740° C. for two hours. After this treatment the white powder obtained had a mean particle diameter of from about 9 microns to about 11.5 microns.

The resulting white powder was silanated by tumbling about 100 g of the white powder with about 4 weight percent silane and 0.5 weight percent acetic acid solution. The mixture or slurry was then dried in an oven in an oven at about 90° C. to obtain Filler Example 5 in powder form.

Physical Characterizations of Filler Materials

TABLE 2

| | Particle Size Distribution by Wet Method (um) |
|---|---|
| Filler Example CTRL1 (Core material) | D10 = 0.26; D50 = 0.43; D90 = 0.71 |
| Filler Example 1 (unsilanated) | D10 = 0.74; D50 = 10.6; D90 = 51.6 |
| Filler Example 2 (silanated) | D10 = 1.08; D50 = 22.9; D90 = 80.9 |

Composite Formulation

Composite Example 1 formulation:

TABLE 3

| Formula | Actual Wt(gm) | Final Wt % paste |
|---|---|---|
| Methacrylic Resin | 20.7 | 25.6 |
| Conventional Filler 0.7 um | 18.0 | 22.3 |
| Filler Example 2 | 31.8 | 39.4 |
| Conventional Filler 0.4 um | 10.3 | 12.7 |
| Total | 80.8 | 100 |

Section V Method to Make the Composite Examples
  Using Ross Mixer
  Procedure for making composite example 1:
  Mix all the filler from Table 3 together for 15 min by using the roller (232 rpm).
  Add about half of the mixed filler, 53 rpm, 50° C., 10 min
  Add about a quarter of the mixed filler, 53 rpm, 50° C., 10 min
  Add about one-sixth of the mixed filler, 53 rpm, 50° C., 10 min
  Scrape the sides and blades, add the remainder of the mixed filler, mix at 53 rpm, 50° C., 10 min
  Scrape the sides and blades, vacuum at 20.0 in Hg, 55 rpm, 50° C., 30 min
  Get the paste out of the pot and put into a suitable container This same method described above, was utilized in creating all composite examples, including those set forth in Table 5.2 below.

Stiffness and Stickiness Measurement Methods
  Stiffness Test Method
  The stiffness of composites was measured by TA XT Plus Texture Analyzer. A 1.7 gram of composite was dispensed into a hole ($\phi16$ mm×4 mm) drilled in a stainless steel plate (4 mm in thickness) which was kept in an environmental chamber with constant temperature of 23° C. The excess amount of composite was removed by a Teflon spatula to make the paste surface even. The cylinder probe ($\phi4$ mm) aligned with the center of the hole started to approach the paste at 5.0 mm/s (pretest Speed) until a 20.0 grams trigger force was detected. The probe then began to compress the paste with a speed of 0.5 mm/s and traveled down a distance of 3 mm. The curve of force vs time was recorded. The slope (gradient) of the curve between 3.5 and 4 seconds was used as an indication of stiffness (kg/sec).

Stickiness Test Method
  The stickiness of composite was measured by TA XT Plus Texture Analyzer. A 0.8 gram of composite was dispensed into a hole ($\phi16$ mm×1.85 mm) drilled in a stainless steel plate (1.85 mm in thickness) which was kept in an environmental chamber with constant temperature of 37° C. The excess amount of composite was removed by a Teflon spatula to make the paste surface even. The probe with a ball-shape tip ($\phi6.32$ mm) aligned with the center of the hole started to approach the paste at 0.5 mm/s (pre-test Speed) until a 5.0 grams trigger force was detected. The probe then began to compress the sample until a load of 1.5 kg was reached. The probe will be kept in the same load for 5 seconds before the probe was withdrawn from the sample at a constant speed of 10.0 mm/s (Post-Test Speed). The separation distance (stringiness/mm) and maximum separation force (kg) of the probe from composite were recorded as indications of stickiness.

Composite Performance Results

TABLE 4.1

|  | Composite Example CTRL1 | Composite Example CTRL2 | Composite Example CTRL3 | Composite Example CTRL4 | Composite Example 1 |
|---|---|---|---|---|---|
| Stiffness (kg/sec) | 0.044 (0.003) | 0.118 (0.013) | 0.065 (0.008) | 0.113 (0.018) | 0.059 (0.005) |
| Stickiness (mm) | 5.66 (1.01) | 1.86 (0.33) | 1.99 (0.30) | 1.65 (0.16) | 0.85 (0.26) |
| Flexure Strength (MPa) | 137.7 (17.5) | 124.3 (15.6) | 120.7 (10.5) | 133.3 (7.1) | 129.6 (8.2) |
| Flexure Modulus (MPa) | 9248 (621) | 10067 (250) | 8530 (418) | 8978 (375) | 10792 (316) |

TABLE 4.2

|  | Comp. Example 1 | Comp. Example 2 | Comp. Example 3 | Composite Example CTRL3 | Composite Example CTRL4 | Composite Example CTRL5 | Composite Example CTRL6 |
|---|---|---|---|---|---|---|---|
| Adjusted Wear Value (mm$^3$) | 0.0057 | 0.0042 | 0.0039 | 0.0073 | 0.0085 | 0.0055 | 0.0057 |

TABLE 4.3

|  | Comp. Example 4 | Composite Example CTRL5 |
|---|---|---|
| Stain by Wine (ΔE) | 1.78 | 3.85 |

It should be noted that according to the data of Table 4.1, composite example 1 greatly improved paste handling features, such as lower the tacky force and stringiness value and at the same time the paste was still soft when the stiffness was from 0.03 kg/sec to about 0.4 kg/sec, or from about 0.07 kg/sec to about 0.12 kg/sec. In Table 4.1, both the flexure strength and flexure modulus were tested using the standardized method set forth in ISO 4049.

The composite example 1 maintained good mechanical strength and polishability.

From Table 4.2, composite example 1 to 3 showed very good wear performance which were better than current HD product and statistically similar to competitive 3M products.

List of Examples

TABLE 5.1

| Example ID | Description |
|---|---|
| Filler Example CTRL1 | 0.4 μm Ba schott glass |
| Filler Example 1 | Unsilanated new agglomerated dental filler |
| Filler Example 2 | Silanated dental filler according to the present disclosure |
| Filler Example 3 | Silanated dental filler according to the present disclosure |
| Filler Example 4 | Silanated dental filler according to the present disclosure |
| Filler Example 5 | Silanated dental filler according to the present disclosure |
| Composite Example CTRL1 | Paste made with 0.7 μm (22.3%) and 0.4 μm glass (52.1%) |
| Composite Example CTRL2 | Paste made with 0.7 μm (61.4%) and 0.4 μm glass (13%) |
| Composite Example CTRL3 | Current Dentsply HD product |
| Composite Example CTRL4 | Current Dentsply HD product |
| Composite Example CTRL5 | 3M Filtek Supreme Ultra |
| Composite Example CTRL6 | 3M Filtek Supreme Ultra |
| Composite Example 1 | Methacrylic resin based paste made with new filler (Filler example 2.), 0.7 μm and 0.4 μm glass |
| Composite Example 2 | Methacrylic resin based paste made with new filler (Filler example 3), 0.7 μm and 0.4 μm glass |
| Composite Example 3 | Methacrylic resin based paste made with new filler (Filler example 4), 0.7 μm and 0.4 μm glass |
| Composite Example 4 | Methacrylic resin based paste made with new filler (Filler example 5), 0.7 μm and 0.4 μm glass |

TABLE 5.2

|  | Composite Example 1 | Composite Example 2 | Composite Example 3 | Composite Example 4 |
|---|---|---|---|---|
| Methacrylic Resin | 25.6 | 23.5 | 25.8 | 24.9 |
| Conventional Filler 0.7 um | 22.3 | 24.1 | 21.9 | 22.4 |

TABLE 5.2-continued

| | Composite Example 1 | Composite Example 2 | Composite Example 3 | Composite Example 4 |
|---|---|---|---|---|
| New Filler | 39.4 Filler 2 | 39.5 Filler 3 | 39.5 Filler 4 | 39.8 Filler 5 |
| Conventional Filler 0.4 um | 12.7 | 12.8 | 12.8 | 12.9 |

It will be appreciated that various of the above-disclosed compositions and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

We claim:

1. An agglomerated filler material comprising a core and a shell,
    wherein the core is made of a core material and the shell is made of a shell material, such that the core material and the shell material are a different material,
    wherein the shell material attaches to the core material via electrostatic forces,
    wherein the core material is positively or negatively charged and the shell material is an opposite charge of the core material,
    wherein a surface area of the agglomerated filler material is from about 1 $m^2/g$ to about 200 $m^2/g$,
    wherein the core material has a particle size of from 300 nm to 2 µm,
    wherein the core material has a greater particle size than the shell material, and
    wherein the agglomerated filler material has a mean particle size of from 600 nm to 50 µm.

2. The agglomerated filler material according to claim 1, wherein the core material is NaO, $K_2O$, $Fe_2O_3$, $SiO_2$, BaO, $Al_2O_3$, $B_2O_3$, $TiO_2$, $ZrO_2$, CaO, MgO, $Y_2O_3$, SrO, $Yb_2O_3$, $SnO_2$, $GeO_2$ or any mixture thereof.

3. The agglomerated filler material according to claim 1, wherein the shell material is NaO, $K_2O$, $Fe_2O_3$, $SiO_2$, BaO, $Al_2O_3$, $B_2O_3$, $TiO_2$, $ZrO_2$, CaO, MgO, $Y_2O_3$, SrO, $Yb_2O_3$, $SnO_2$, $GeO_2$ or any mixture thereof.

4. The agglomerated filler material according to claim 1, wherein at least one of the core material or the shell material further includes fluorine.

5. The agglomerated filler material according to claim 1, wherein the agglomerated filler material is heated to a temperature of from 500° C. to 900° C.

6. The agglomerated filler material according to claim 1, wherein the agglomerated filler material is silanated to a level of from 0.1% to 20%.

7. The agglomerated filler material according to claim 1, wherein the shell material has a particle size of from 1 nm to 300 nm.

8. A dental material comprising a resin, an initiator system, and an agglomerated filler material, wherein the agglomerated filler material comprises a core and a shell,
    wherein the core is made of a core material and the shell is made of a shell material, such that the core material and the shell material are a different material,
    wherein the shell material attaches to the core material via electrostatic forces,
    wherein the core material is positively or negatively charged and the shell material is an opposite charge of the core material,
    wherein a surface area of the agglomerated filler material is from about 1 $m^2/g$ to about 200 $m^2/g$,
    wherein the core material has a particle size of from 300 nm to 2 µm,
    wherein the core material has a greater particle size than the shell material, and
    wherein the agglomerated filler material has a mean particle size of from 600 nm to 50 µm.

9. The dental material according to claim 8, wherein the resin is an acrylic resin, a methacrylic resin, an epoxy resin, a vinyl resin, a urethane resin or a combination thereof.

10. The dental material according to claim 8, wherein the filler material is present in an amount of 20% to 90% of the dental material.

11. The dental material according to claim 8, wherein the dental material include a second filler material.

12. The dental material according to claim 11, wherein the filler material comprising the core and the shell comprises at least 10% by weight of a total filler mixture.

13. The dental material according to claim 8, wherein the filler material is silanated to a level of from 0.1% to 20%.

14. The dental material according to claim 8, wherein the core material is NaO, $K_2O$, $Fe_2O_3$, $SiO_2$, BaO, $Al_2O_3$, $B_2O_3$, $TiO_2$, $ZrO_2$, CaO, MgO, $Y_2O_3$, SrO, $Yb_2O_3$, $SnO_2$, $GeO_2$ or any mixture thereof.

15. The dental material according to claim 8, wherein the shell material is NaO, $K_2O$, $Fe_2O_3$, $SiO_2$, BaO, $Al_2O_3$, $B_2O_3$, $TiO_2$, $ZrO_2$, CaO, MgO, $Y_2O_3$, SrO, $Yb_2O_3$, $SnO_2$, $GeO_2$ or any mixture thereof.

16. The agglomerated filler material according to claim 1, wherein the agglomerated filler material has a mean particle size of from 5 µm to 25 µm.

17. The dental material according to claim 8, wherein the agglomerated filler material has a mean particle size of from 5 µm to 25 µm.

* * * * *